United States Patent [19]

Nakamura et al.

[11] Patent Number: 4,606,996

[45] Date of Patent: Aug. 19, 1986

[54] METHOD OF REDUCING TREATMENT OF SILVER HALIDE PHOTOGRAPHIC LIGHT-SENSITIVE MATERIAL FOR PHOTOCHEMICAL PROCESS

[75] Inventors: Taku Nakamura; Yasuo Kasama; Yasuo Mukunoki, all of Kanagawa, Japan

[73] Assignee: Fuji Photo Film Co., Ltd., Kanagawa, Japan

[21] Appl. No.: 803,800

[22] Filed: Dec. 3, 1985

Related U.S. Application Data

[63] Continuation of Ser. No. 620,772, Jun. 14, 1984, abandoned.

[30] Foreign Application Priority Data

Jun. 17, 1983 [JP] Japan .............................. 58-108690

[51] Int. Cl.$^4$ ................................................ G03C 7/00
[52] U.S. Cl. ...................................... 430/309; 430/430; 430/432; 430/523; 430/961
[58] Field of Search ............... 430/309, 430, 432, 427, 430/523, 950, 961

[56] References Cited

U.S. PATENT DOCUMENTS

| | | |
|---|---|---|
| 4,021,244 | 5/1977 | Nagatomo et al. ................ 430/950 |
| 4,047,957 | 9/1977 | DeWinter et al. ................ 430/961 |
| 4,198,478 | 4/1980 | Yoneyama et al. ................ 430/449 |
| 4,264,719 | 4/1981 | Kameoka et al. ................ 430/950 |
| 4,292,402 | 9/1981 | Pollet et al. ................ 430/950 |
| 4,330,618 | 5/1982 | Minamizono et al. ............. 430/961 |
| 4,343,894 | 8/1982 | Minamizono et al. ............. 430/961 |
| 4,362,812 | 12/1982 | Minamizono et al. ............. 430/961 |
| 4,374,924 | 2/1983 | Yokoama et al. ................ 430/923 |
| 4,399,213 | 8/1983 | Watanabe et al. ................ 430/950 |
| 4,460,680 | 7/1984 | Ogawa et al. ................ 430/961 |
| 4,476,218 | 10/1984 | Ogawa et al. ................ 430/961 |
| 4,533,623 | 8/1985 | Urata et al. ................ 430/309 |

*Primary Examiner*—Jack P. Brammer
*Attorney, Agent, or Firm*—Sughrue, Mion, Zinn, Macpeak & Seas

[57] ABSTRACT

A silver halide photographic light-sensitive material for photomechanical process is described, comprising a support, at least one photosensitive silver halide emulsion layer thereon, and at least one light-insensitive upper layer on the emulsion layer. At least one of the light-insensitive upper layers contains a compound having an electric charge and being substantially insoluble in water but soluble in a water-miscible organic solvent; a method for a reducing treatment is also described, which comprises bringing a silver image formed on the light-sensitive material into contact with a reducer through the light-insensitive upper layer containing the aforesaid compound.

7 Claims, No Drawings

METHOD OF REDUCING TREATMENT OF SILVER HALIDE PHOTOGRAPHIC LIGHT-SENSITIVE MATERIAL FOR PHOTOCHEMICAL PROCESS

This is a continuation of application Ser. No. 620,772 filed 6/14/84 now abandoned.

FIELD OF THE INVENTION

This invention relates to a silver halide photographic light-sensitive material for photomechanical process, and to a method for reducing treatment using the same.

BACKGROUND OF THE INVENTION

In the graphic arts industries and the like, a light-sensitive material to make an original transparency signifies light-sensitive materials which are used for converting continuous-tone images of originals into halftone images or for photographing line originals or the like, which is involved in a photomechanical process.

In the usual production of printing plates utilizing such light-sensitive materials as described above, partial or overall minute retouch of image is carried out. This is done with the intention of reproducing the delicate tones of originals so that they have excellent printing characteristics or satisfying the artistic expression of the printed image. This is frequently carried out by subjecting these materials to a processing referred to as a reduction processing. This involves reducing the dot area of halftone images, or increasing or decreasing the width of line images, or so on.

Accordingly, whether or not the light-sensitive material has an aptitude for a reduction processing has become very important of such materials.

To subject a light-sensitive material for photomechanical process having a halftone image or a line image formed thereon through an exposure and development process, a method is used which comprises contacting metallic silver forming the halftone or line image with a reducer. Many kinds of reducers are known. For example, Mees, *The Theory of the Photographic Process*, pages 738-739 (1954, Macmillan Co.) describes reducers containing permanganates, ferric salts, ceric salts, potassium ferricyanide, persulfates and bichromates as reducing components.

Since the reducing treatment is after all the oxidation and dissolving of a silver image, when the dot area of a halftone image is decreased by the reducing treatment, the blackening density of the dots is simultaneously decreased. Accordingly, the range modifiable by the reducing treatment is restricted by the degree of decrease of the blackening density per dot which occurs during the decreasing of the dot area. In other words, the measure of the modifiable range of a halftone image can be expressed by the extent of the decrease of the dot area which can be effected while the blackening density per dot is maintained above a certain fixed value.

The extent to which the dot area has been decreased from that before treatment is determined when as a result of the reducing treatment, the blackening density of a dot is decreased to a minimum limit required in the photomechanical process, and this is expressed in the present specification as the "reduction extent". The larger the reduction extent, the higher is the adaptability of the light-sensitive material for photomechanical process to the reducing treatment.

As a technique for increasing adaptability to a reducing treatment, a method involving using a reducer containing a mercapto compound during the reducing treatment is known, as described, for example, in Japanese Patent Application (OPI) No. 68419/1977 (the term "OPI" as used herein refers to a "published unexamined Japanese patent application"). The reducer thereof is special and difficult to use, because the rate of reduction differs from those of reducers generally used. If an emulsion film is rendered soft and the covering power and the density are increased, it is possible to increase the reduction extent and improve the reducing treatment characteristics. However, this method cannot provide the generally required film strength.

From a technical viewpoint, the most effective method among the techniques of increasing the reduction extent and improving the reducing treatment adaptability that have been known is to increase the amount of silver forming an image. This is because the modifiable range of the image by the reduction treatment becomes broader as the amount of silver forming the silver image per unit area is larger. Accordingly, the reduction extent can be broadened by increasing the amount of silver halide used in a light-sensitive material for photomechanical process per unit area. However, as is well known, silver is very expensive and valuable, thus increasing the amount of silver coated is undesirable in view of the cost of the resulting light-sensitive material for photomechanical process.

It is, therefore, one of the important problems in the art to produce light-sensitive materials for photomechanical process having desirable reducing characteristics as noted above while using as little silver as possible.

Japanese Patent Application (OPI) No. 42039/1983, by the present applicant, has proposed that in order to solve the above problem, a light-insensitive upper layer having a longer melting time than the melting time of a silver halide emulsion layer be formed on the silver halide emulsion layer. By this means, the reducing treatment adaptability of the resulting light-sensitive material can be greatly improved without increasing the amount of silver coated. However, in order to increase the melting time of the light-insensitive upper layer, it must be hardened independently of the emulsion layer. Hence, it has been found that the coating of this layer is not sufficiently easy and care must be taken, or reticulation occurs.

SUMMARY OF THE INVENTION

It is a first object of this invention to provide a light-sensitive material for photomechanical process having improved adaptability to a reducing treatment.

A second object of this invention is to provide a light-sensitive material for photomechanical process whose adaptability to a reducing treatment is not deteriorated even when the amount of silver coated per unit area is decreased.

A third object of this invention is to provide a light-sensitive material for photomechanical process having improved adaptability to a reducing treatment which can be obtained by an easy coating operation without the occurrence of reticulation.

A further object of this invention is to provide a method of reducing treatment which can attain a large extent of reduction with a light-sensitive material for photomechanical process having a small amount of silver coated per unit area.

These objects of the invention are achieved by a light-sensitive material for photomechanical process comprising a support, at least one photosensitive silver halide emulsion layer thereon, and at least one light-insensitive upper layer on the emulsion layer, at least one of the light-insensitive upper layers containing a compound having an electric charge and being substantially insoluble in water but soluble in a water-miscible organic solvent; and by a method for a reducing treatment, which comprises bringing a silver image formed on the light-sensitive material for photomechanical process by exposure and development into contact with a reducer through the light-insensitive upper layer containing the compound.

DETAILED DESCRIPTION OF THE INVENTION

It is not known exactly why the present invention brings about an improvement in the performance of the reducing treatment. However, since a compound having no electric charge is not effective, it presumably has something to do with the fact that the charge density of the light-insensitive upper layer becomes larger than that of the emulsion layer by the addition of the compound specified in this invention.

The term "light-insensitive upper layer" as used herein means a layer composed of a hydrophilic colloid and having no photosensitive silver halide and is positioned above the photosensitive silver halide emulsion layer.

The term "charge" as used herein means that compounds are anionic (such as sulfonic acids, carboxylic acids, phosphoric acids, and salts thereof, etc.), cationic (such as primary, secondary, tertiary and quaternary ammonium salts, guanidine salts, imidine salts, etc.), or amphoteric (such as sulfobetaine, carboxybetaine, etc.). Anionic and amphoteric compounds are preferred, especially the former.

The compound as used in this invention is substantially insoluble in water but soluble in a water-miscible organic solvent. The expression "substantially insoluble in water" as used herein means that the solubility in water at 25° C. is not more than 0.1% by weight; according to a preferred embodiment, it is not more than 0.05% by weight. The expression "soluble in a water-miscible organic solvent" means that the solubility in a water-miscible organic solvent at 25° C. is at least 1% by weight; according to a preferred embodiment of the invention, the solubility in the water-miscible organic solvent is at least 3% by weight.

Accordingly, in the present invention, a compound is used which has a charge and a hydrophobic portion that is sufficient for a loss of solubility in water as a whole.

Preferred as such a compound are low molecular weight compounds having both a hydrophobic group having at least 16 carbon atoms and an —SO$_3$M or —OSO$_3$M group (in which M represents a monovalent cation) in each molecule; such compounds are described in U.S. Pat. No. 3,525,620, Ryohei Oda and Kazuhiro Teramura, Synthesis and Application of Surface Active Agents (Japanese language publication published by Maki Shoten, Japan), and A. W. Perry, Surface Active Agents, Interscience Publications Inc., New York.

Examples include the following compounds.

$$C_{16}H_{33}SO_3Na \quad (A-1)$$

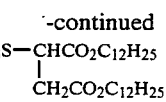

(A-2)

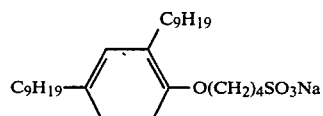

(A-3)

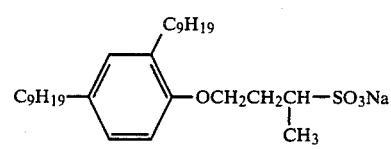

(A-4)

Other examples include polymers containing at least 5 mol % of a unit represented by formula (I):

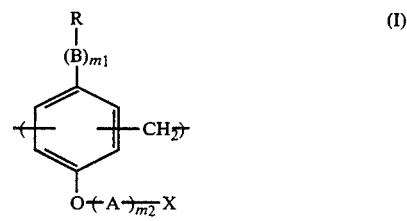

(I)

wherein R represents an aliphatic hydrocarbon group having from 4 to 22 carbon atoms; $m_1$ and $m_2$ represent each 0 or 1; B represents —O— or —NH—; A represents an aliphatic divalent group having from 1 to 50 carbon atoms; and X represents a functional group having an electric charge, especially a sulfonic acid group.

The aliphatic hydrocarbon group having from 4 to 22 carbon atoms represented by R in formula (I) may be linear or branched, and may contain an unsaturated bond. Preferably, R has from about 6 to 18 carbon atoms. Examples of R include alkyl groups such as butyl, octyl, nonyl, dodecyl, and octadecyl, and alkenyl groups such as cis-9-octadecenyl.

Preferably, the aliphatic divalent group having from 1 to 50 carbon atoms represented by A includes alkylene groups, alkyleneoxy groups, polyalkyleneoxy groups and alkyleneoxy-alkylene groups. Specific examples include ethylene, trimethylene, octamethylene, ethyleneoxy, polyethyleneoxy, polypropyleneoxy and ethyleneoxy-trimethylene groups.

X is especially preferably the —SO$_3$M group in which M represents a cation. Examples of the cation represented by M include hydrogen, soidum, potassium, lithium, calcium, barium, ammonium, and alkylammoniums having from 1 to 4 carbon atoms.

The polymers used in this invention contain at least 5 mol %, and preferably at least 10 mol %, of the unit represented by formula (I).

The polymers may be homopolymers or copolymers. The copolymers contain about 5 to 95 mol %, and preferably about 10 to 60 mol %, of the unit represented by formula (I). At least one unit copolymerizable with the unit of formula (I) can be used. The unit to be copolymerized therewith is a divalent unit composed of a benzene ring having a methylene group or a naphthalene ring having a methylene group. The benzene ring or naphthalene ring may be substituted by substituents; for example, alkyl groups preferably having from 4 to 22 carbon atoms, such as butyl, octyl, nonyl, dodecyl and octadecyl groups; halogen atoms such as chlorine, bromine and iodine atoms; a hydroxyl group; alkoxy groups preferably having from 4 to 22 carbon atoms, such as octyloxy, hexyloxy, dodecyloxy and beta-hydroxyethoxy groups; and haloalkoxy groups preferably having from 4 to 22 carbon atoms, such as beta-chloroethoxy and beta-bromoethoxy groups. Preferably, it is substituted by at least one substituent.

Examples of the units to be copolymerized therewith are shown below.

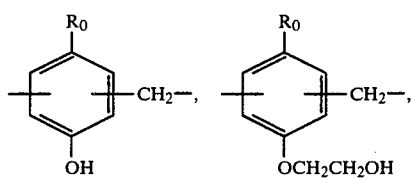

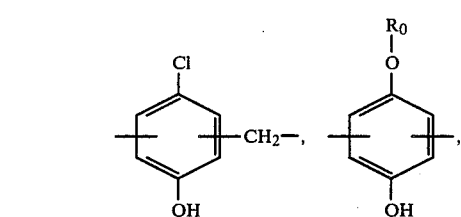

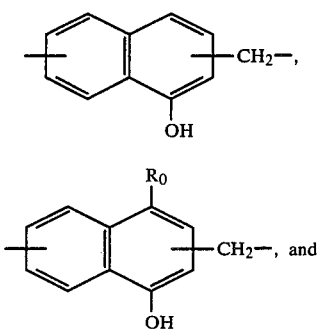

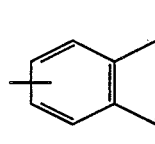

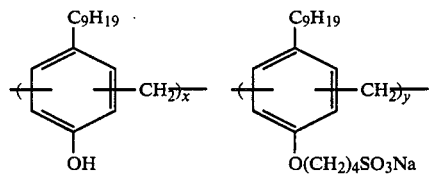

In the above formulae, $R_0$ represents an aliphatic hydrocarbon group having from 4 to 22 carbon atoms.

The molecular weight of the polymers used in this invention is not particularly limited. Preferably, it is from about 600 to about 10.000, and especially preferably it is from 900 to 5,000.

Specific examples of typical polymers that can be used in this invention are set forth below.

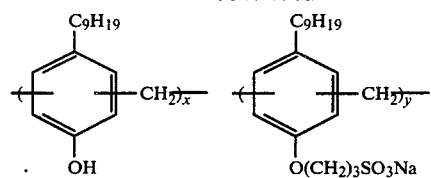 (B-1)

x:y = 58:42, x + y ≈ 6
The term "≈" means an average value of "x + y" or "w + x + y + z".

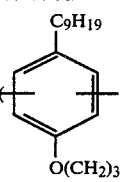 (B-2)

x:y = 60:40, x + y ≈ 6

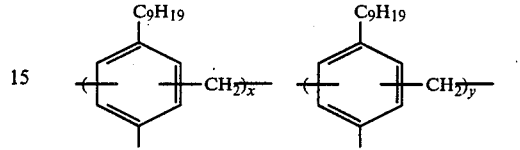 (B-3)

x:y = 80:20, x + y ≈ 6

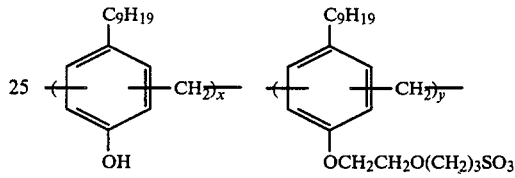 (B-4)

x:y = 50:50, x + y ≈ 6

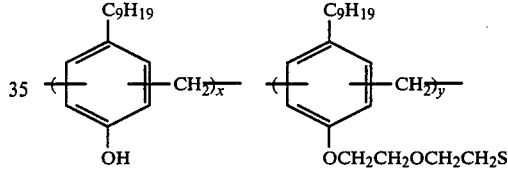 (B-5)

x:y = 80:20, x + y ≈ 10

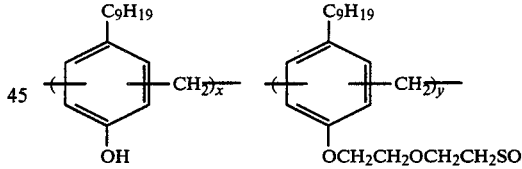 (B-6)

x:y = 80:20, x + y ≈ 25

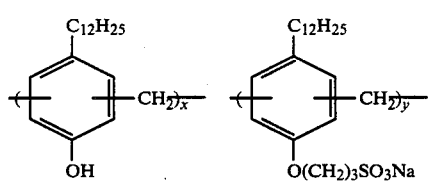 (B-7)

x:y = 60:40, x + y ≈ 10

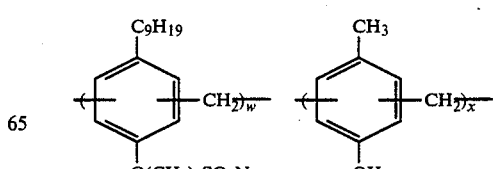 (B-8)

-continued

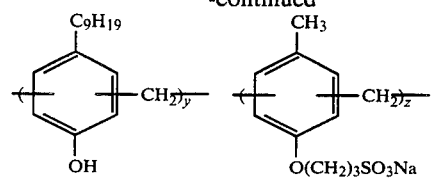

(w + ):(x + y) = 50:50, w + x + y + z ≈ 5

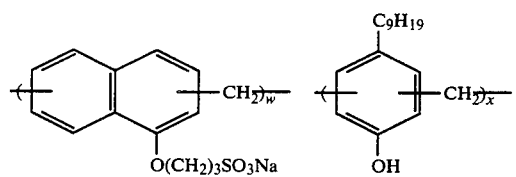

(B-9)

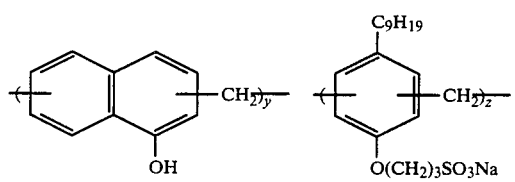

(w + z):(x + y) = 40:60, w + x + y + z ≈ 8

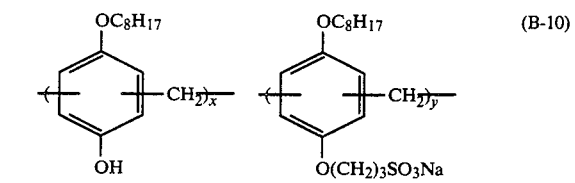

(B-10)

x:y = 60:40, x + y ≈ 8

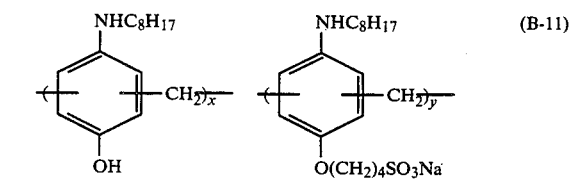

(B-11)

x:y = 50:50, x + y ≈ 4

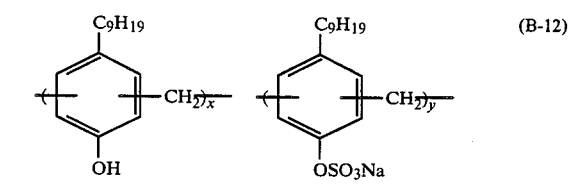

(B-12)

x:y = 60:40, x + y ≈ 6

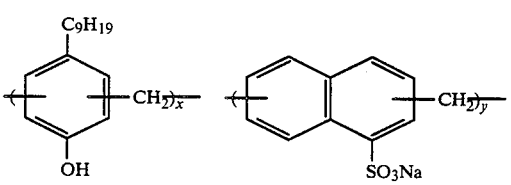

(B-13)

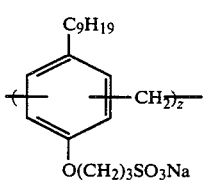

-continued x:y:z = 40:30:30, x + y + z ≈ 6

Polymers represented by formula (II) can also be used as the compound specified in the present invention:

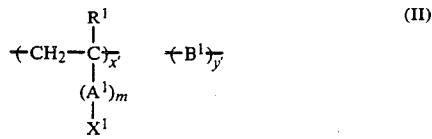

(II)

wherein $R^1$ represents a hydrogen atom, a halogen atom (such as Br or Cl), or a lower alkyl group (such as a methyl, ethyl, or butyl group); $A^1$ represents a divalent connecting group (such as a phenylene, alkylene or alkylenecarbamoyl group); $X^1$ represents a functional group having an electric charge (such as a sulfonic acid group); m is 0 or 1; x' is from 10 to 90 mol %, and preferably from 20 to 50 mol %; $B^1$ represents a monomer unit having copolymerized therewith a water-insoluble monomer having one ethylenically unsaturated bond; and y' is from 10 to 90 mol %, and preferably from 50 to 80 mol %.

Specific examples of $B^1$ include monomer units having copolymerized therewith styrene, styrene derivatives, alkyl acrylates or alkyl methacrylates.

Examples of preferred polymers of formula (II) are shown below.

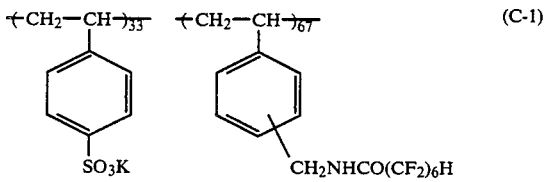

(C-1)

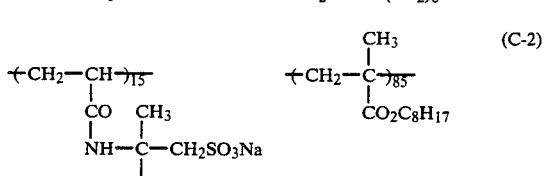

(C-2)

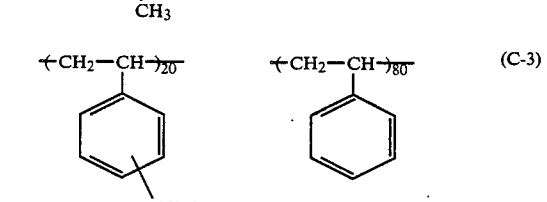

(C-3)

Among the compounds described above, polymers containing at least 5 mol % of the unit of formula (I) are especially preferred.

The compound of this invention is formed into an aqueous dispersion by dissolving it in a water-miscible organic solvent, mixing the solution with an aqueous solution of a hydrophilic colloid for the light-insensitive upper layer, optionally together with a surface active agent, with stirring. Accordingly, the compound of this invention is immobilized in the light-insensitive upper layer and is hard to transfer into the emulsion layer.

Examples of the water-miscible organic solvent include organic solvents miscible with water in arbitrary ratios, for example, lower alcohols such as methanol and ethanol, acetone, dimethylformamide and dimethyl sulfoxide; and organic solvents miscible with water in a weight of at least 10%, for example, n-butanol, water-soluble ketones such as methyl ethyl ketone, and lower fatty acid esters such as ethyl acetate.

The amount of the compound used in accordance with this invention is determined for each compound by considering its effect on the reduction extent and its influence on the reduction time. Generally, favorable results can be obtained by using it in an amount of from about 2 to 150% by weight, and preferably it is used in an amount of from about 10 to 60% by weight, based on the weight of the hydrophilic colloid in the light-insensitive upper layer.

The light-sensitive material for photomechanical process in this invention is a light-sensitive material used in the printing industry for printing halftone images or line images by a photomechanical process, and is not particularly limited in kind and performance. The generally used light-sensitive material is a high-contrast light-sensitive material such as a so-called lith film.

Accordingly, there is no particular limitation on the silver halide used in the photosensitive silver halide emulsion layer of the light-sensitive material for photomechanical process of this invention. For example, silver chlorobromide, silver chloroiodobromide, silver iodobromide and silver bromide can be used. Silver chlorobromide or silver chloroiodobromide containing at least 60 mol %, and preferably at least 75 mol %, of silver chloride, and 0 to 5 mol % of silver iodide, is preferred. The form, crystal habit, size distribution, etc., of the silver halide grains are not particularly restricted, but the grain size is preferably not more than 0.7 micron.

The sensitivity of the silver halide emulsion can be increased, without making its grains coarse, by using a reducing substance, for example, a gold compound such as a chloroaurate or gold trichloride, a salt of a noble metal such as rhodium or iridium, a sulfur compound capable of forming silver sulfate upon reaction with a silver salt, a stannous salt, or an amine.

It is also possible to use a salt of a noble metal such as rhodium or iridium, potassium ferricyanide, etc., during the physical ripening of the silver halide grains, or during the formation of a nucleus.

Gelatin can be advantageously used as the hydrophilic colloid binder used in the emulsion layer, the light-insensitive upper layer or other layers in the light-sensitive material for photomechanical process of this invention. Other hydrophilic colloids may also be used.

Examples of the other hydrophilic colloids include proteins such as gelatin derivatives, graft polymers of gelatin with other polymers, albumin and casein; cellulose derivatives such as hydroxyethyl cellulose, carboxymethyl cellulose and cellulose sulfate esters; sugar derivatives such as sodium alginate and starch derivatives; and various synthetic hydrophilic polymers such as polyvinyl alcohol, a partially acetalized product of polyvinyl alcohol, poly-N-vinyl-pyrrolidone, polyacrylic acid, polymethacrylic acid, polyacrylamide, polyvinylimidazole and polyvinylpyrazole and the corresponding copolymers.

Gelatin may be lime-treated gelatin, acid-treated gelatin, or the enzyme-treated gelatins described in Bull. Soc. Scie. Phot., Japan, No. 16, page 30 (1966). Hydrolyzed or enzymatically decomposed products of gelatin can also be used.

For the purpose of increasing the dimensional stability of the light-sensitive material, improving film properties, etc., the silver halide emulsion layer or other layers may contain polymer latexes composed of homopolymers or copolymers of alkyl acrylates, alkyl methacrylates, acrylic acid, glycidyl acrylate, etc., which are described in U.S. Pat. Nos. 3,142,568, 3,325,286, 3,411,911, 3,411,912, and 3,547,650 and Japanese Patent Publication No. 5331/1970.

As antifogging agents for the emulsion, there can be used, for example, 4-hydroxy-6-methyl-1,3,3a,7-tetraazaindene, 3-methylbenzothiazole, 1-phenyl-5-mercaptotetrazole, many other heterocyclic compounds, mercury-containing compounds, mercapto compounds, and antifogging agents well known in the art as described, for example, in Japanese Patent Application (OPI) Nos. 81024/1974, 6306/1975 and 19429/1975 and U.S. Pat. No. 3,850,639.

Examples of hardeners that may be used in this invention include aldehyde compounds, ketone compounds, compounds having reactive halogen such as 2-hydroxy-4,6-dichloro-1,3,5-triazine, compounds having reactive olefin such as vinylsulfone-type compounds, N-methylol compounds, aziridine compounds, and carbodiimide compounds.

Surface active agents may be added to the silver halide emulsion layer in this invention as a coating aid or in order to improve photographic properties.

Examples of preferred surface active agents include natural surface active agents such as saponin; nonionic surface active agents such as the alkylene oxide and glycidol types; anionic surface active agents containing acidic groups such as a carboxyl group, a sulfo group (e.g., the surface active agents described in U.S. Pat. No. 3,415,649), a phospho group, a sulfate group, or a phosphate group; and amphoteric surface active agents such as amino acids, aminosulfonic acids, and sulfate or phosphate esters of aminoalcohols.

The polyalkylene oxide compounds used in this invention include condensation products of at least 10 units of a polyalkylene oxide of an alkylene oxide having from 2 to 4 carbon atoms such as ethylene oxide, propylene-1,2-oxide and butylene-1,2-oxide, preferably ethylene oxide, and a compound containing at least one active hydrogen atom such as water, an aliphatic alcohol, an aromatic alcohol, a fatty acid, an organic amine or a hexitol, or block copolymers of at least two kinds of polyalkylene oxides. Thus, specifically, polyalkylene oxide compounds that can be used are polyalkylene glycols, polyalkylene glycol alkyl ethers, polyalkylene glycol aryl ethers, polyalkylene glycol alkylaryl esters, polyalkylene glycol esters, polyalkylene glycol fatty acid amides, polyalkylene glycol amines, polyalkylene glycol block copolymers, and polyalkylene glycol graft polymers.

Specific examples of polyalkylene oxide compounds that can be preferably used in this invention are listed below.

1. $HO(CH_2CH_2O)_9H$
2. $C_{12}H_{25}O(CH_2CH_2O)_{15}H$
3. $C_8H_{17}CH{=}CHC_8H_{16}O(CH_2CH_2O)_{15}H$
4.

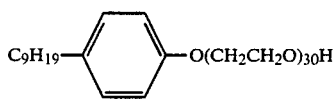

5. $C_{11}H_{23}COO(CH_2CH_2O)_{80}H$
6. $C_{11}H_{23}CONH(CH_2CH_2O)_{15}H$
7.

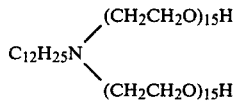

8. $C_{14}H_{29}N((CH_2)(CH_2CH_2O)_{24}H$
9.

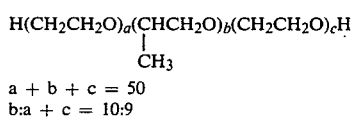

a + b + c = 50
b:a + c = 10:9

The weight ratio of the silver halide to the hydrophilic colloid binder in the silver halide emulsion layer in this invention is preferably ½ or less.

In this invention, the number of the silver halide emulsion layers is not limited to 1, and may be or more.

For example, when there are two silver halide emulsion layers, the total weight ratio of silver halide to hydrophilic colloid polymer in the two layers is ½ or less. Preferably, the upper emulsion layer contains more hydrophilic colloid binder than the lower emulsion layer.

The amount of silver halide coated is preferably from 1.0 to 6.0 g, and more preferably from 1.5 to 4.0 g, per m² calculated as silver.

The effect of this invention is especially remarkable when the amount of silver coated is small.

The light-insensitive upper layer in this invention may include a surface active agent, an antistatic agent, a matting agent, a lubricant, colloidal silica, a gelatin plasticizer, a polymer latex, etc., in addition to the hydrophilic colloid binder (such as gelatin).

Polymethyl methacrylate and silicon dioxide in a particle diameter of from 0.1 to 10 microns, and particularly about 1 to 5 microns, are preferred as the matting agent.

A polyester film such as a polyethylene terephthalate film and a cellulose ester film such as a cellulose triacetate film are preferably used as the support of the light-sensitive material for photomechanical process of this invention.

Imagewise exposure to obtain an image may be carried out by ordinary methods. There can be used various light sources such as natural light (sunlight), a tungsten lamp, a fluorescent lamp, a mercury vapor lamp, a xenon lamp, an arc lamp, a carbon arc light, a xenon flash lamp and a cathode ray tube flying spot. The exposure time may be from 1/1,000 second to 1 second employed in ordinary cameras. Of course, the exposure time may be shorter than 1/1,000 second, for example, from $1/10^4$ to $1/10^6$ second, by using a xenon flash lamp or a cathode ray tube, or longer than 1 second. As required, the spectral composition of light used for exposure may be adjusted by a color filter. A laser light can also be used for exposure. There is no particular restriction on the method of developing the light-sensitive material for photomechanical process of this invention, and methods which are usually employed for processing light-sensitive materials for photomechanical process can be used. The processing temperature is usually selected between 18° C. and 50° C., but may be lower than 18° C. or higher than 50° C.

The developing solution may contain any known developing agent selected, for example, from dihydroxybenzenes (such as hydroquinone), 3-pyrazolidones (such as 1-phenyl-3-pyrazolidone), aminophenols (such as N-methyl-p-aminophenol), 1-phenyl-3-pyrazolines, ascorbic acid, and the heterocyclic compounds in which a 1,2,3,4-tetrahydroquinoline ring is fused with an indolenine ring as described in U.S. Pat. No. 4,067,872, either singly or in combination. The developing solution generally contains known preservatives, alkaline agents, pH buffers, antifogging agents, etc., and optionally a dissolution aid, a toning agent, a development promoter, a surface active agent, a defoaming agent, a water softening agent, a hardener, a viscosity imparting agent, etc.

A lithographic developing solution is especially preferred for use in this invention. Basically, it is composed of o- or p-dihydroxybenzene, an alkaline agent, and a small amount of a free sulfite salt, a small amount of a sulfite ion buffer, etc. The o- or p-dihydroxybenzene as a developing agent can be properly selected from those well known in the photographic field. Specific examples include hydroquinone, chlorohydroquinone, bromohydroquinone, isopropylhydroquinone, toluhydroquinone, methylhydroquinone, 2,3-dichlorohydroquinone and 2,5-dimethylhydroquinone. Of these, hydroquinone is particularly practical.

These developing agents may be used singly or as a mixture. The amount of the developing agent is 1 to 100 g, preferably 5 to 80 g, per liter of the developing solution. The sulfite ion buffer is used in an amount effective for maintaining the concentration of the sulfite salt in the developing solution at a nearly fixed value. Examples of the sulfite ion buffer are aldehyde/alkali hydrogen sulfite adducts such as formaldehyde/sodium hydrogen sulfite adduct, ketone/alkali hydrogen sulfite adducts such as acetone/sodium hydrogen sulfite adduct, and carbonyl bisulfite/amine condensation products such as sodium-bis(2-hydroxyethyl)aminomethane sulfonate. The amount of the sulfite ion buffer used is generally from 13 to 130 g per liter of the developing solution.

The free sulfite ion concentration of the developing solution used in this invention may be adjusted by adding an alkali sulfite such as sodium sulfite. The amount of the sulfite is generally not more than 5 g (although it may be larger), and preferably not more than 3 g, per liter of the developing solution.

In many cases, it is preferred to include an alkali halide (especially a bromide such as sodium or potassium bromide) as a development control agent. The amount of the alkali halide is preferably from 0.01 to 10 g, and especially preferably from 0.1 to 5 g, per liter of the developing solution.

An alkaline agent is added to adjust the pH of the developing solution to at least 9, and preferably to from 9.7 to 11.5. Sodium carbonate or potassium carbonate in varying amounts may be used as the alkaline agent as in normal developing solutions.

A fixing solution of a conventional composition may be used.

Thiosulfates, thiocyanates, and organic sulfur compounds known to have an effect of a fixing agent may be used as the fixing agent.

The fixing solution may contain a water-soluble aluminum salt as a hardener. A customary method can be applied when a color image is to be formed.

The development may be carried out by a hand operation or by using an automatic processor. When the automatic processor is to be used, there is no particular restriction on the method of conveying (for example, roller conveying, belt conveying, etc.), and any conveying-type automatic processor used in the art can be used. For the composition of the processing solution and the method of development, reference may be made to the disclosures of U.S. Pat. Nos. 3,025,779, 3,078,024, 3,122,086, 3,149,551, 3,156,173, 3,224,356 and 3,573,914. For the silver halide emulsion layer, the other layers and the support of the light-sensitive material for photomechanical process of this invention, the method of processing it, etc., reference may be made to the description of Research Disclosure, Vol. 176, pages 22–28, December 1978.

There is no particular limitation on the reducer used in this invention. For example, there can be used the reducers described in Mees, The Theory of the Photographic Process, pages 738–739 (1954), Tetsuo Yano, Photographic Processing, Its Theory and Application (Japanese language publication published by Kyoritsu Shuppan K.K., Japan, 1978), and Japanese Patent Application (OPI) Nos. 27543/1975, 140733/1976, 68429/1977, 14901/1978, 119236/1979, 119237/1979, 2245/1980, 2244/1980, 17123/1980, 79444/1980, and 81344/1980.

Specifically, reducers may be used containing permanganates, persulfates, ferric salts, cupric salts, ceric salts, potassium ferricyanide and bichromate salts either alone or in combination as an oxidizing agent and as required, an inorganic acid such as sulfuric acid and an alcohol, or reducers containing such an oxidizing agent as potassium ferricyanide or ferric ethylenediaminetetraacetate, a solvent for silver halide such as a thiosulfuric acid salt, a rhodanate, thiourea or derivatives thereof, and as required, an inorganic acid such as sulfuric acid.

Typical examples of the reducer used in this invention include the Farmer's reducer, a ferric ethylenediaminetetraacetate reducer, a potassium permanganate/ammonium persulfate reducer (e.g., Kodak R-5), and a ceric salt reducer.

The light-sensitive material of this invention for photomechanical process is especially effective for a reducing treatment with a ceric salt reducer. Thus, the use of a reducer containing toxic potassium ferricyanide is no longer necessary. This is one advantage of this invention.

The ceric salt reducer usually contains from 10 to 130 g, especially 20 to 70 g, per liter of the reducer of a ceric salt such as ceric sulfate, ceric acetate, ceric ammonium nitrate and ceric potassium nitrate, and an acid (either an organic or inorganic acid such as sulfuric acid, nitric acid, phosphoric acid or acetic acid; the preferred amount is not more than 1.0N per liter of the reducer) and as required, an alcohol, a glycol, a mercapto compound, a surface active agent, or a thickener (such as hydroxyethyl cellulose).

The reducing treatment is generally carried out at from 10° to 40° C., and preferably at from 15° to 30° C., and is preferably completed within several seconds to several tens of minutes, preferably within several minutes. With the light-sensitive material for photomechanical process of this invention, a sufficiently large reduction extent can be obtained under these reducing conditions.

The reducer acts on the silver image formed in the emulsion layer through the light-insensitive upper layer containing the compound specified in this invention. This can be effected by various methods. For example, the light-sensitive material for photomechanical process can be immersed in the reducer and the reducer is stirred. Or the reducer can be applied to the surface of the light-insensitive upper layer side of the light-sensitive material for photomechanical process by a brush, a roller, etc.

The following Examples illustrate the present invention more specifically.

EXAMPLE 1

A silver halide emulsion composed of 80 mol % silver chloride, 19.5 mol % silver bromide and 0.5 mol % silver iodide was prepared in the customary manner using gold sensitization and sulfur sensitization. The amount of gelatin contained in the emulsion was 45% by weight.

3-Carboxymethyl-5-[2-(3-ethylthiazolinylidene)ethylidene]rhodanine (spectral sensitizer), 4-hydroxy-1,3,3a,7-tetraazaindene (stabilizer), polyoxyethylene nonyl phenyl ether containing 50 ethylene oxide groups, and the polymer latex described in Production Recipe 3 of Japanese Patent Publication No. 5331/1970 (corresponding to U.S. Pat. No. 3,525,620) were successively added to the emulsion. Then, N,N-ethylene-bis(-vinylsulfonylacetamide) was added as a hardener in the amount indicated below to prepare a coating solution for forming a silver halide emulsion light-sensitive layer.

In the meantime, each of the compounds of this invention indicated in Table 1 was added as shown in Table 1 to form a coating solution for a light-insensitive upper layer.

The two coating solutions were coated on a polyethylene terephthalate film support to prepare a sample. The amount of silver coated was 2.6 g per m², and the amount of gelatin coated in the light-insensitive upper layer was 1.0 g per m².

TABLE 1

| Sample No. | Amount of the Hardener (g/m$^2$) | Compound (amount added, g/m$^2$) | Degree of Swelling (H$_2$O, 25° C.)* | Remarks |
| --- | --- | --- | --- | --- |
| 1 | 0.063 | — | 1.10 | Control |
| 2 | " | B-1 (0.172) | 1.07 | Invention |
| 3 | " | B-1 (0.344) | 1.28 | Invention |
| 4 | " | B-1 (0.516) | 1.23 | Invention |
| 5 | " | A-3 (0.21) | 1.08 | Invention |
| 6 | " | A-3 (0.31) | 1.11 | Invention |

*Degree of swelling

The ratio of the thickness of the coated layer dipped in water at 25° C. (thickness $d+\Delta d$ to that (d) of the layer at 25° C. and 60% RH, i.e., $(d+\Delta d/d)$, is defined as the degree of swelling.

A halftone image was formed in the resulting sample by the following procedure.

A commercially available gray contact screen (150 lines/inch) for negatives was brought into close contact with the sample, and the sample was exposed for 10 seconds to a white tungsten light through a step wedge having a step difference of 0.1. The exposed sample was developed with a lithographic developing solution having the following formulation at 20° C. for 3 minutes, and fixed, washed and dried in the customary manner.

| Developer Solution | |
| --- | --- |
| Sodium Carbonate | 50 g |
| Formaldehyde/Hydrogen Sulfite Adduct | 45 g |
| Potassium Bromide | 2 g |
| Hydroquinone | 18 g |
| Sodium Sulfite | 2 g |
| Water to make | 1 liter |

The resulting halftone strips were dipped in a reducer of the following formulation for 20 to 100 seconds with stirring and then washed with water.

| Reducer | |
| --- | --- |
| Ceric Sulfate | 25 g |
| Concentrated Sulfuric Acid | 30 g |
| Water to make | 1 liter |

Changes in the dot area of the resulting half-tone strips and changes in density for each dot were measured by a microdensitometer.

Dots of the halftone strips which has a dot area of 50% were subjected to the reducing treatment until the density of each of the dots became 2.5. The dot area of the halftone strips at this time, and the reducing time required for it, and the reduction extent are summarized in Table 2.

TABLE 2

| Sample No. | Before Reduction Dot Area (dot density) | After Reduction Dot Area (dot density) | Reducing Time (seconds) | Reduction Extent (%) |
| --- | --- | --- | --- | --- |
| 1 | 50% (above 4.0) | 43.3% (2.5) | 36 | 6.1 |
| 2 | 50% (above 4.0) | 39.9% (2.5) | 50 | 10.1 |
| 3 | 50% (above 4.0) | 38.1% (2.5) | 80 | 11.9 |
| 4 | 50% (above 4.0) | 40.9% (2.5) | 36 | 9.1 |
| 5 | 50% (above 4.0) | 42.0% (2.5) | 33 | 8.0 |
| 6 | 50% (above 4.0) | 42.9% (2.5) | 30 | 6.9 |

It is seen from Table 2 that when Sample Nos. 2 to 6 containing the Compounds B-1 and A-3 of this invention are treated with the reducer containing ceric sulfate as an oxidizing agent, a large reduction extent can be obtained, The reducing time was somewhat long, but still suitable.

EXAMPLE 2

The same samples as in Example 1 were used, and subjected to a reducing treatment using a reducer of the following formulation.

| Reducer | |
| --- | --- |
| Ferric Sodium Ethylenediaminetetraacetate | 85 g |
| Thiourea | 65 g |
| Citric Acid | 60 g |
| Hydrochloric Acid | (amount sufficient to adjust the pH to 1.0) |
| Water to make | 1 liter |

The results are shown in Table 3.

TABLE 3

| Sample No. | Before Reduction Dot Area (dot density) | After Reduction Dot Area (dot density) | Reducing Time (seconds) | Reduction Extent (%) |
| --- | --- | --- | --- | --- |
| 1 | 50% (above 4.0) | 44.3% (2.5) | 45 | 5.7 |
| 2 | 50% (above 4.0) | 42.2% (2.5) | 57 | 7.8 |
| 3 | 50% (above 4.0) | 39.3% (2.5) | 58 | 10.7 |
| 4 | 50% (above 4.0) | 39.6% (2.5) | 67 | 10.4 |

It is seen from Table 3 that when the Sample Nos. 2 to 4 containing the Compound B-1 in accordance with this invention are treated with Fe-EDTA type reducer, the reduction extent is large although not as large as in the case of using the ceric salt reducer.

As Examples 1 and 2 demonstrate, by including the compound having at least one electric charge and being substantially insoluble in water and soluble in a water-miscible organic sovlent in at least one light-insensitive upper layer, the reduction extent in a reducing treatment can be increased, and the adaptability of the light-sensitive material for photomechanical process to reduction can be greatly improved.

While the invention has been described in detail and with reference to specific embodiments thereof, it will be apparent to one skilled in the art that various changes and modifications can be made therein without departing from the spirit and scope thereof.

What is claimed is:

1. A method for reducing treatment of a silver halide photographic light-sensitive element for a photomechanical process wherein said photographic light-sensitive element comprises a support, at least one photosensitive silver halide emulsion layer thereon, and at least one light-insensitive upper layer on the emulsion layer, wherein said light-insensitive upper layer comprises a hydrophillic colloid and at least one of the light-insensitive upper layers contains a compound having an electric charge and is substantially insoluble in water but soluble in a water-miscible organic solvent, wherein said compound is employed in am amount sufficient for increasing adaptability to a reducing treatment and wherein said compound is a polymer containing at least 5 mol % of a unit represented by formula (I):

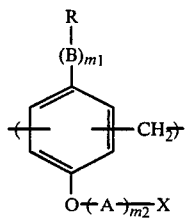 (I)

wherein R represents an aliphatic hydrocarbon group having from 4 to 22 carbon atoms; $m_1$ and $m_2$ represent each 0 or 1; B represents —O— or —NH—; A represents an aliphatic divalent group having from 1 to 50 carbon atoms; and X represents a functional group having an electric charge, said method comprising bringing a silver image, formed on the light-sensitive element by exposure and development, into contact with a reducer through said light-insensitive upper layer containing said compound.

2. The method as claimed in claim 1, wherein said compound has a solubility in water at 25° C. of not more than 0.01% by weight, and a solubility in a water-miscible organic solvent at 25° C. of at least 1% by weight.

3. The method as claimed in claim 1, wherein said polymer is a copolymer containing from about 10 to 60 mol % of the unit represented by formula (I).

4. The method as claimed in claim 1, wherein said compound is used in an amount of from about 2 to 150% by weight based on the weight of the hydrophillic colloid in the light-insensitive upper layer.

5. The method as claimed in claim 1, wherein said compound is used in an amount of from about 10 to 60% by weight based on the weight of the hydrophillic colloid in the light-insensitive upper layer.

6. The method as claimed in claim 1, wherein said water-miscible organic solvent is selected from the group consisting of lower alcohols, acetone, dimethylformamide, dimethyl sulfoxide, n-butanol, water-soluble ketones and lower fatty acid esters.

7. The method as claimed in claim 1, wherein said compound having an electric charge is selected from the compounds which contain an anionic charge, a cationic charge and an amphoteric charge.

* * * * *